United States Patent
MacNeil

(10) Patent No.: US 6,899,294 B2
(45) Date of Patent: May 31, 2005

(54) HATCHERY EGGSHELL WASTE PROCESSING METHOD AND DEVICE

(75) Inventor: Joseph Herman MacNeil, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 102 days.

(21) Appl. No.: 10/276,850

(22) PCT Filed: Mar. 30, 2001

(86) PCT No.: PCT/US01/10518

§ 371 (c)(1),
(2), (4) Date: Nov. 19, 2002

(87) PCT Pub. No.: WO01/74491

PCT Pub. Date: Oct. 11, 2001

(65) Prior Publication Data

US 2003/0209617 A1 Nov. 13, 2003

Related U.S. Application Data

(60) Provisional application No. 60/194,296, filed on Apr. 3, 2000.

(51) Int. Cl.[7] .............................................. B02C 17/00
(52) U.S. Cl. .............................. 241/24.12; 241/24.16; 241/27; 241/68; 241/81; 426/480; 426/518
(58) Field of Search ..................... 241/24.1, 24.11, 241/24.12, 24.16, 24.26, 26, 27, 29, 68, 69, 77, 81; 426/299, 479, 480, 518; 209/44, 44.1, 510

(56) References Cited

U.S. PATENT DOCUMENTS 4,187,989 A * 2/1980 McAleer et al. ............... 241/2
5,199,380 A    4/1993 Keromnes et al.
5,415,875 A    5/1995 Kakoki et al.
6,176,376 B1 * 1/2001 MacNeil ..................... 209/510
6,649,203 B1 * 11/2003 Thoroski ..................... 426/299

FOREIGN PATENT DOCUMENTS

| EP | 601698 | 6/1994 | |
|---|---|---|---|
| JP | 59-49878 | * 3/1984 | ........... B01D/21/01 |
| JP | 60-259160 | * 12/1985 | ................... 426/74 |
| JP | 03045264 | 2/1991 | |
| JP | 03255018 | 11/1991 | |
| JP | 04169513 | 6/1992 | |
| JP | 60259160 | 12/1995 | |
| WO | PCT/NL97/00072 | 8/1997 | |
| WO | PCT/US98/05315 | 9/1998 | |
| WO | PCT/US01/06720 | 9/2001 | |

* cited by examiner

*Primary Examiner*—Ed Tolan
(74) *Attorney, Agent, or Firm*—McQuaide, Blasko, Schwartz, Fleming & Faulkner, Inc.

(57) ABSTRACT

A method and apparatus for separating the organic membrane portion of waste egg shells from the hard inorganic mineral portion thereof, so that each can be used or further processed as desired, thereby addressing the environmental and economic issues associated with disposing of waste egg shells. The membrane and shell are separated by first processing waste eggshells so as to yield small waste eggshell particles. During this processing, the waste eggshell particles are at least slightly abraded, whereby the linking structure between the membrane and shell is at least partially disrupted. Thereafter, the waste eggshell particles are conveyed to a device, which isolates the two components based on their size and weight differences. The methods listed above can provide products from the eggshell waste including precipitated calcium carbonate, membrane, protein, amino acids, collagen and other important components.

34 Claims, 4 Drawing Sheets

Hatchery Waste Shells from Hatchery Waste

Hatchery Waste Shells from Hatchery Waste

Figure 1:
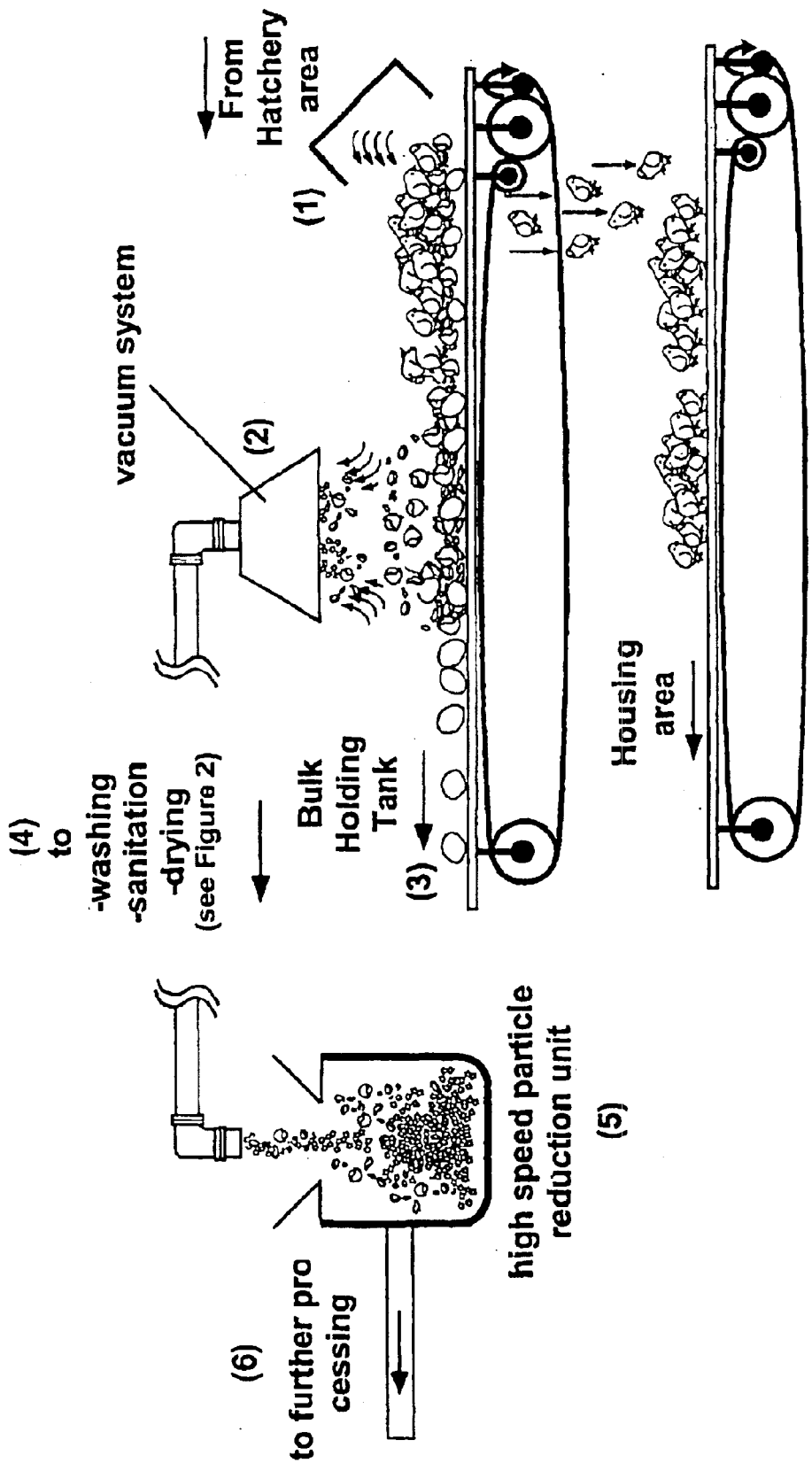

Shaker Belt Separation of Membrane and Shell

Hatchery Waste Shell Processing Flow Chart

HATCHERY EGGSHELL WASTE PROCESSING METHOD AND DEVICE

This application claims benefit of provisional application 60/194,296 file Apr. 3, 2000.

FIELD OF THE INVENTION

This invention relates to a method and apparatus for separating and recovering the shell and non-shell (e.g., membrane) components from hatchery waste.

BACKGROUND

According to the United Egg Producers Association figures for year 2000 there were 484,000,000 Egg-type chicks ("layers") eggs set by hatcheries in the U.S. Using their 90% hatchability rate this would result in the production of 435,600,000 waste eggshells. Broiler production industry figures for 2000 showed that 7,800,000,000 eggs were set and with a hatchability rate of 82% this resulted in slightly over 6 billion waste shells.

In addition, the use of eggs by the processed egg sector ("breaker eggs") during 2000 totaled approximately 1.7 billion (USDA Egg Products Summary, 2000). Breaker eggs are used as ingredients in other processed foods and various food service operations. For example, the albumen ("egg white") and egg yolk may be recovered to manufacture liquid egg products of various types. In other instances, the albumen and egg yolk may be dried to form a more shelf-stable product (e.g., powdered eggs). In the latter case, the waste egg shells amassed from such processing are usually subjected to further processing (e.g., such as with a centrifuge) in order to recover residual albumen which adheres to the egg shells, which can be sold to the pet food industry.

Even after processing of the breaker egg waste to remove excess albumin, in the year 2000, egg breaking companies in the U.S., produced approximately 13,000 tons of eggshell waste.

Hatchery waste is more difficult to handle than breaker shell since it consists of (a) shells from the hatched chicks (b) unhatched eggs that contain dead embryos and (c) unhatched eggs that were infertile. The hatchability rate for broiler chicks is about 82% while the hatchability for layers is around 90%. The latter situation reflects fewer infertile and dead embryos. The mixed waste (b) and (c) above from hatcheries is either disposed of at the hatchery's expense or recycled by the hatchery company into a feed supplement. Based on the numbers above, which showed approximately 6.5 billion eggs being produced by the hatchery industry, roughly 50,000 tons of eggshell waste is generated which must be disposed of.

A survey conducted in 1997 in collaboration with the United Egg Producers indicated that almost 50% of U.S. egg processors each generate 1000 to 3000 tons of eggshell waste each year. Among the survey respondents, 26.6% used the egg shell waste as fertilizer, 21.1% used it as a feed ingredient, 26.3% disposed of it in dumps as waste, and 15.8% put it to "other" use(s). Among the respondents identifying disposal costs, almost three-quarters reported disposal costs between $25,000 and $100,000 per year.

In view of the significant disposal costs for what is conventionally a waste product, and additionally, in view of current environmental practicalities which are decreasing the availability of local disposal sites (thereby further increasing disposal cost), it will be readily appreciated that finding a significant use for egg shell waste would have important financial and environmental benefits.

It is well known that the eggshell of the chicken is a biologic composite of organic matrix (membrane) and inorganic mineral (shell). The mineral of the shell is mainly calcitic calcium carbonate. The shell membranes remain non-mineralized throughout the assembly of the eggshell and the development of the embryo (Wyburn et al., 1970, Exp. Physiology 55:213). Between the shell and the membrane is a layer of foci of mineralized matrix called the calcium reserve assembly (CRA). The CRA provides the mobilized calcium for the mineralization of the skeleton of the developing embryo (Diekert et al., 1989, Poultry Science 68:1569). At the apex of each CRA is a region known as the crown The crown is a morphologically distinct structure where function is not clear. It may act to separate the resorbable calcium (CRA) and non-resorbable calcium (shell). External to the crown is the shell proper, which is approximately 250 mm in thickness and contains approximately 5 gm of calcium carbonate (Diekert et al., 1989, Poultry Science 68:1569) It is this part of the shell which acts to physically encase and protect the developing embryo (Arias et al., 1991, Matrix 11:313).

Knowledge of the various eggshell structures was critical in developing procedures for recovering and separating eggshell calcium material from the membrane. With breaker eggs, the CRA is still intact after the breaking process. This material provides a very strong bond between the shell and membrane making the separation of shell and membrane very difficult. In contrast, the waste hatchery shell has essentially no CRA left because the developing embryo absorbs the calcium from the CRA, thus destroying the bond between the membrane and the shell (calcium carbonate). During hatchery shell receiving, the membranes separate from the shell as they move along the chick harvesting belt. This phenomenon contributes to a very simple separation procedure.

Two shell membranes surround the egg of most avian species. A thick outer membrane attached to the shell and a thin inner-membrane. Each of these membranes is composed of a network of fibers. Early studies suggested that collagen was present as indicated by hydroxylysine and the digestion of eggshell membrane by collagenase. The presence of Type I and Type V collagen were established in the membrane by Wong (Wong et al., 1984, Developmental Biology 104:28) and Arias (Arias et al., 1991, Matrix 11:313) Other studies (Leach et al., 1982 Poultry Science 61:2040) showed that a unique protein containing lysine-derived cross links was present. Recent studies have identified, among other constituents, type V and X collagen and proteoglycans (mammillan, a keratan sulfate proteoglycan, and ovoglycan, a dermatan sulfate proteoglycan), whose localization depends on a topographically defined and temporally regulated deposition. (Soledad F. et al., 2001, Matrix Biol. 19:793).

The presence of collagen in the shell membranes is noteworthy because of the increasing demand for collagen. Bovine, and to a lesser extent, human, collagen is becoming relatively common and is used in a variety of applications, especially in the biomedical field. For example, a collagen glue made from human collagen is known for filling corneal wounds. Also, research is ongoing in producing skin and tissue replacement products made from collagen. Type X collagen appears throughout both shell membranes. Recent research has shown that Type X Collagen is responsible for prohibiting mineralization of the shell membranes (Sorensen, J., Podiatry Today 1995) and could play a major role in the prevention and treatment of osteoporosis or in the use of arterial transplants where the major reason for failure is calcification of the transplanted valve.

Unfortunately, the cost of such collagen based products is very high (at least about $1,000 per gram, or about $454,000 per pound), although such costs are considered economically acceptable, at least in medical applications, in view of the overall cost of medical treatment.

In addition, use of bovine collagen raises an issue as to the possible transmission of bovine borne diseases, including e.g. bovine spongiform encephalopathy (commonly known as "mad cow disease"). Although the risk of mad cow disease transmission is currently considered very small in this country, the mere perception of possible risk creates a need for private, well-isolated, and expensive herds.

Another problem with bovine collagen is the risk of autoimmune and allergic reactions caused thereby, since approximately 2% to 3% of the population are allergic in this regard. Although, this would appear to be a small percentage, the problem is likely to increase, as the use of bovine collagen products becomes more common.

In summary, a central issue in waste egg disposal is the fact that it is a mixed waste consisting of organic and inorganic components from which it has been difficult, especially in the case of hatchery waste, to extract products of residual value. Eggshell waste is commonly disposed of at the expense of industry and to the detriment of the environment. If practicable processing and recycling methods were available, the reduction of the waste disposal burden would provide important financial and environmental benefits. All totaled, there is a heretofore theoretical potential to recover from the U.S. egg industry more than 55,000 tons of calcitic calcium carbonate from the shell which can be used as pure calcium supplement source for use as a nutritional supplement product such as pills, fruit drinks, cookies other pastries, dairy products, salad sprinkles, cereal and many other food products. In addition, over 5000 tons of membrane, composed of protein, collagen and other components, is available for recovery and recycling (See Table 1 for comparison of protein from egg membrane and other protein sources).

SUMMARY OF THE INVENTION

This invention involves a method and device for separately recovering the shell and non-shell components from hatchery eggshell waste. The invention simultaneously diminishes the environmental impact associated with waste eggshell disposal while offering economic benefit from use of the resultant products.

One approach of this invention which is especially useful for hatchery waste shells involves the steps of: (a) providing an initial mixture of hatchery waste shells; (b) processing the initial mixture to reduce its particle size, or, dislodge at least part of the membrane from the eggshell thereof, or, in many cases depending on the sort of equipment used, to effect both results together, to yield a processed eggshell waste mixture, and, (c) separately recovering the shell components, one or more non-shell components or both, from the processed eggshell waste mixture.

A second approach is also provided which is of greatest interest for separately recovering the shell and non-shell components specifically from breaker eggshell waste. This method involves the steps of: (a) providing an initial mixture of breaker waste shells; (b) processing the initial mixture to reduce its particle size, or, dislodge at least part of the membrane from the eggshell thereof, or, in many cases depending on the sort of equipment used, to effect both results together, to yield a processed eggshell waste mixture; and, (c) separately recovering the shell components, one or more of the non-shell components or both, from processed eggshell waste mixture wherein the initial waste or one or more of the processed wastes can be treated to reduce its moisture content.

In both methods, the initial mixture can be processed using a particle size reduction apparatus, which mechanically reduces particle size. Many such apparatuses are known, are commercially available, and are widely used for reducing particle size of a variety of materials. Thus, for example, the initial mixture could be processed using a slicer, dicer, strip cutter, shredder, grinder, granulator, mill, comminutor, abrader, pulverizer, crusher, compactor, blender or sonicator apparatus. A particularly useful example of a particle size-reducing device useful in practicing the present invention is commercially available from Urschel Laboratories Inc. under the trademark "Comitrol". Comitrol devices are well known and widely used for particle size reduction, especially in food processing.

In one embodiment of the invention, the initial mixture of hatchery waste shells can be obtained from a mixture of chicken hatchery waste by the separation of hatchery waste shell material from materials other than those of hatched eggshell origin. For example, a particularly useful method is to position a vacuum suction system over the area where the chicks are being harvested. After removal of the chicks, the suction force power is adjusted so that the dry, very light shells from the hatched eggs are retrieved preferentially over other debris. For instance, dead embryos and infertile eggs, being significantly heavier than the pieces of shell, would not be picked up by the suction system and would be separately transferred elsewhere for disposal, e.g., by transfer to a wet bulk disposal tank.

In another embodiment of the invention, the initial mixture of shells from hatchery waste is washed and sanitized (e.g. by chemical, heat, radiation, ultrasonic means) at any point or points throughout the process prior to processing the initial mixture to remove part or all of any residual materials other than those of eggshell origin. In fact any or all of the devices described herein can be configured to be food preparation grade e.g. meeting the USDA requirements for hygiene and sanitation. Optionally, it may be useful to dry the hatchery waste shell mixture following the washing step. A drying step will often be preferable before the separate isolation of the shell and membrane components. Drying is defined as a reduction of moisture content to less than 50% by weight, preferably less than 10% by weight, more preferably less than 2% by weight, relative to starting weight.

In the method of this invention, the shell and non-shell components are typically separately recovered based on their respective differences in physical properties. For example, the heavier shell and lighter non-shell components can be separately recovered from one another using a vibrating or shaking device (e.g. a shaker-sieve belt) to separate relatively larger, lighter or less dense components from smaller, heavier or denser components. Alternatively, the shell and non-shell components can be separately recovered using a stream of gas to separate relatively larger, lighter or less dense components from smaller, heavier or denser components. An example of such a device is a cyclone forced-air separator. A variety of devices useful to effect such separations in the practice of this invention are well known, commercially available and widely deployed in the processing of chemical, food and agricultural products.

The separately recovered shell component can be washed if desired to remove part or all of any residual non-shell materials. Such processing can yield a composition containing purified calcitic calcium carbonate with trace amounts of avian products, suitable for human consumption.

It may also be useful to sanitize and/or sterilize (e.g. by chemical, heat, radiation or ultrasonic treatment means) the separated shell and non-shell components, especially to a degree permitting use of such products in, or consumption by, humans under USDA and US FDA requirements.

Also provided is a device for separately recovering the shell and non-shell components from eggshell waste. Such device comprises at least three components: a delivery apparatus (a) for providing an initial mixture of waste shells to a processing apparatus (b); the processing apparatus (b) for processing the initial mixture to (i) reduce its particle size, or, (ii) dislodge at least part of the membrane from the eggshell thereof, or, (iii) both (I) and (ii), to yield a processed eggshell waste mixture; and, (c) a separation apparatus (c) for separately recovering the shell components, the non-shell components or both, from the processed eggshell waste mixture.

Figure 2:
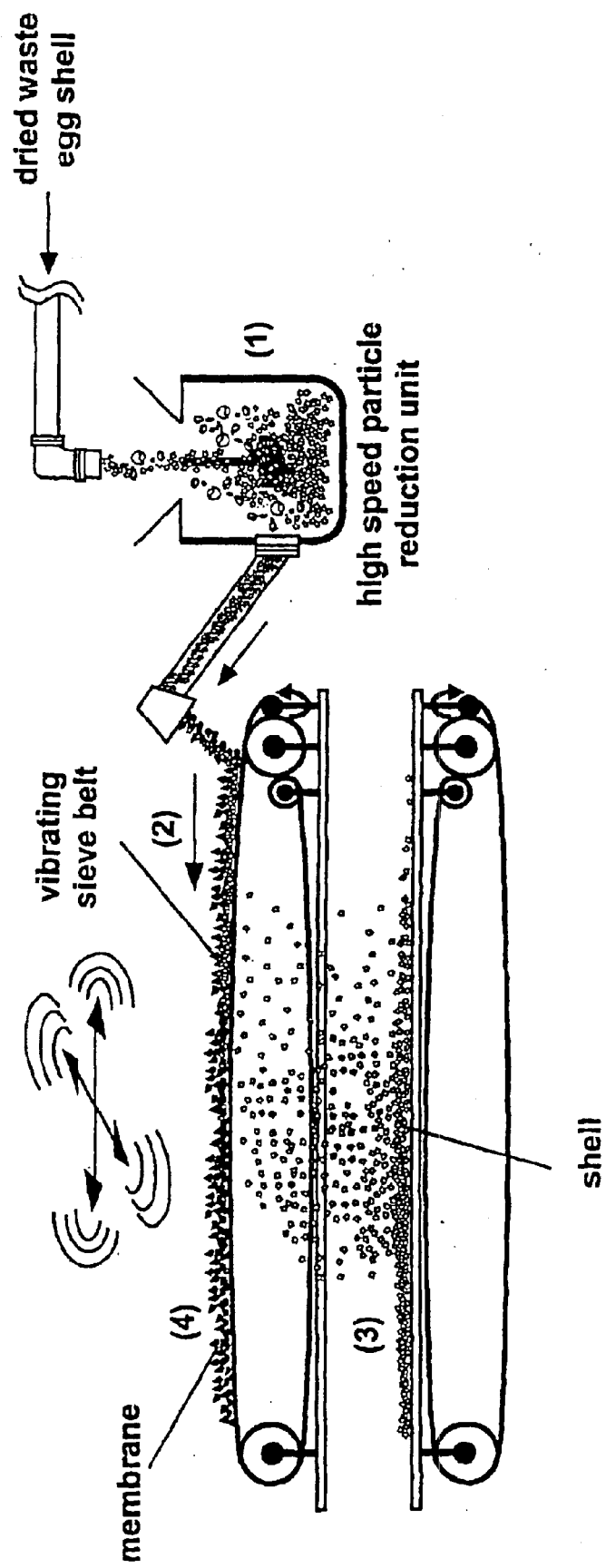

The delivery apparatus of the device may be, e.g., a feed tube, conveyor apparatus or storage apparatus disposed for delivery of the initial mixture of eggshell waste to the processing apparatus. In some cases, it is a storage apparatus linked by an auger to the processing apparatus (via optional washing, sanitizing and/or drying apparatuses) as depicted in FIG. 2.

The device may further comprise a moisture reducing apparatus disposed either between the processing apparatus and the separation apparatus or between the delivery apparatus and the processing apparatus.

The processing apparatus (b) of the device will be, as alluded to earlier, an apparatus, which mechanically reduces particle size. A wide variety of such apparatuses which may be adapted to the present invention are well known and include an apparatus such as a slicer, dicer, strip cutter, shredder, grinder, granulator, mill, comminutor, abrader, pulverizer, crusher, compactor, blender or sonicator apparatus. Of particular interest are Comitrol® Processors.

In some cases, the device further contains a separation apparatus utilizing a vacuum suction disposed prior to the delivery apparatus for separating hatched waste shell material from materials other than those of hatched eggshell origin.

The device may further include a washing apparatus disposed between the delivery apparatus and the processing apparatus, for washing an initial mixture of waste shells to remove part or all of any residual materials other than those of eggshell origin prior to processing the initial mixture.

The separation apparatus (c) may be any apparatus, which can separate shell, and non-shell components based on their respective differences in physical properties. Examples were noted previously, including a vibrating or shaking device, like a shaker sieve belt, or a gas-stream-based device like a cyclone forced-air separator It should also be noted that the device may have a washing apparatus disposed after the separation apparatus (c) for removing part or all of any residual non-shell materials from the separately recovered shell component, and/or a sterilizing apparatus disposed after the separation apparatus (c) for sterilizing one or more of the separately recovered components.

Significantly, this invention provides economically feasible means for recovering various avian collagen products from the separately recovered non-shell component. In view of the methods and apparatus disclosed herein, it now becomes practical for the first time to separately isolate avian collagen(s) (e.g. collagen I, V and X) and other high value products (e.g. calcitonin, tocopherol, vitamins and individual amino acids) from egg shell waste using otherwise conventional methods, and to provide compositions containing one or more of those materials in highly purified form, suitable for use in humans or for human consumption, even though the compositions may contain trace amounts of one or more other identifiable avian materials.

BRIEF DESCRIPTION OF THE DRAWINGS AND TABLE

The present invention will become more fully understood from the detailed description given hereinbelow and the accompanying drawings which are given by way of illustration only, and thus are not limitative of the present invention and wherein:

FIG. 1

Figure 3:
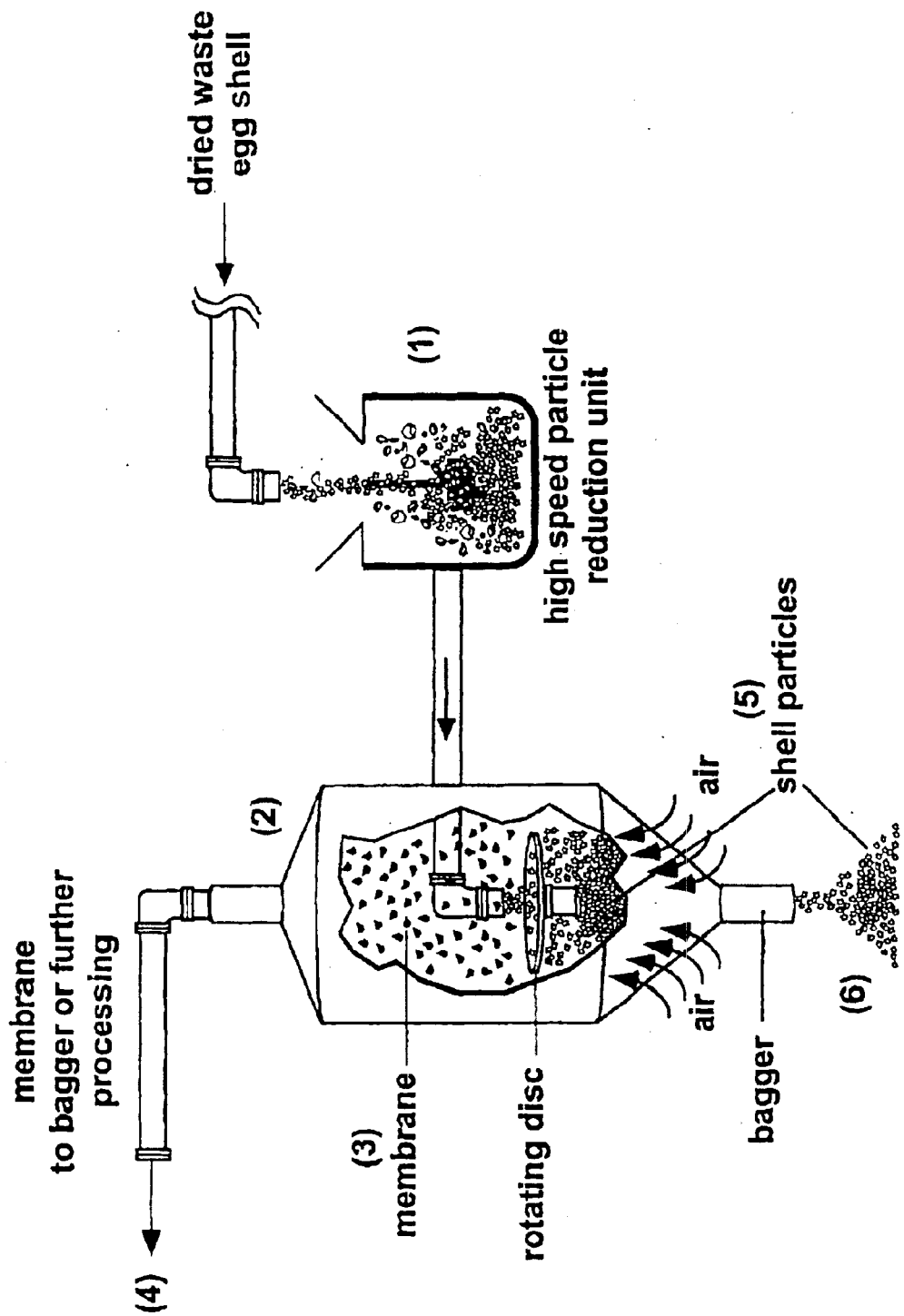
Figure 4:
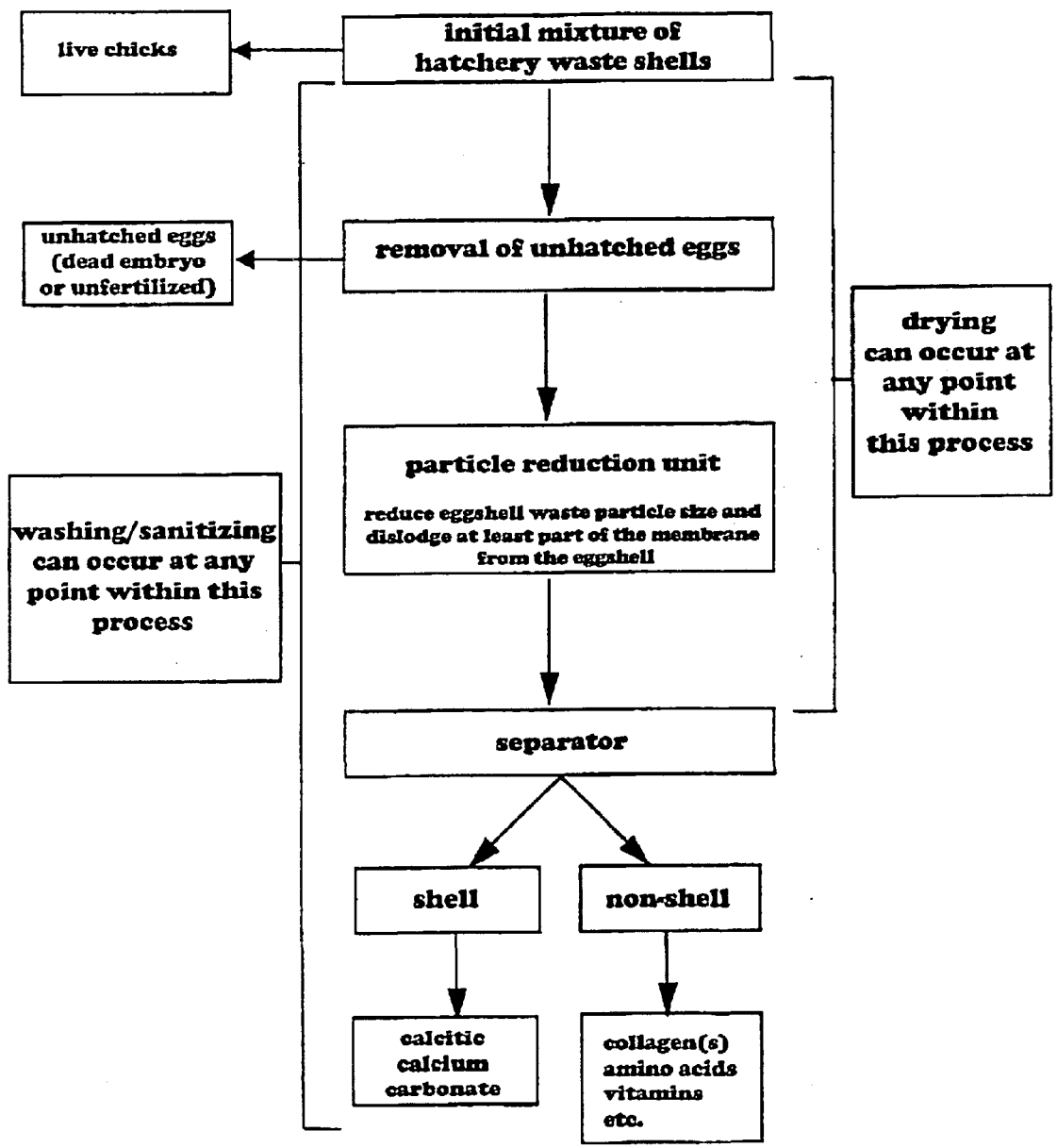

Harvesting Waste Shells from Hatchery Waste. This figure illustrates a harvesting procedure starting with a mix of live chicks, broken shells and unhatched eggs (infertile or dead embryo). (1) Trays of live chicks, broken shells and unhatched eggs are dumped onto a moving belt, which has fixed gaps that allow chicks to fall through but retain broken shells and unhatched eggs. The chicks are conveyed to a housing area and the shell waste continues on towards the vacuum system (2). Here, the broken shell is vacuumed up leaving the unhatched eggs to proceed (3) on the conveyor to bulk holding tanks where they will be processed for animal food. The broken shell waste is first washed, sanitized, dried (4) and then transferred to the high-speed particle reduction unit (5) where the shell is physically separated from the membrane. The mixture of membrane and shell is then sent on for further processing (6) (see FIGS. 2 and 3).

FIG. 2

Shaker Separation of Membrane and Shell. This figure shows a shaker/separation belt (2) receiving the mixture of shell and membrane from the high-speed particle reduction unit (1). The shaker/separation belt is not a continuous belt but a vibrating belt, which moves the product along while screening the product. The heavier, smaller shell will drop through the screen onto a conveyor (3) where it can be bagged or be further processed. The membrane remains on the top belt (4) where it can also be collected for further processing.

FIG. 3

Air Separation of Membrane and Shell. This figure shows a cyclone-type forced air separator (2) receiving the mixture of shell and membrane from the high-speed particle reduction unit (1). The lighter membrane (3) is conveyed by air up in the separator to a bagger or for further processing (4). The heavier shell (5) drops down and can be removed from the bottom of the separator to a bagger or for further processing (6).

FIG. 4

Flow chart for Hatchery Egg Waste Processing. This is an illustrative flowchart outlining a method for hatchery egg waste processing.

DETAILED DESCRIPTION

The foregoing and other objectives of the present invention will become more apparent from the detailed description given hereinafter. However, it should be understood that the detailed description and specific examples, while indicating embodiments of particular interest, are given by way of illustration and example only, since various changes and modifications within the spirit and scope of the invention will become apparent to those skilled in the art from this detailed description.

The present invention will be described herein below with reference to the drawings appended hereto.

Egg Waste Processing

In a standard egg-breaking plant, egg trays are placed on the breaking machine where they are automatically broken. A combination of mechanical and pneumatic equipment processes the eggs quickly and efficiently. Washing and breaking is carried out automatically in-line. The liquid egg fraction is automatically separated from the waste eggshell. From here, shell material can be fed automatically into a standard centrifuge used for liquid retrieval. Egg breaker waste has a significant liquid component comprised of the residual yolk and white of the egg. This wet eggshell waste could first be subjected to centrifugation to remove the excess liquid. This material has significant nutritional value and can be used as a food supplement. For example, a Model C-430: continuous centrifuge from Coenraadts is already being used in the egg breaking industry in order to recuperate the egg white remaining in the shells and to reduce the volume of the shells simultaneously. From there, a screw-type auger can be used to move the spun shells to a washer/sanitizer. In this case, a standard Single-Motion blender used to mix liquid/solid mixtures produced by Lee Industries in Philipsburg, Pa., could be used to wash and sanitize the shells. These units are specifically designed for blending liquids, liquids with particles of varying densities, solids that may be easily damaged and other similar processes. Other brands and designs of blenders could of course be substituted. The agitator configuration of the washer assures that particles or other liquids are folded into the total batch and provides a folding, rolling action rather than just pushing the product as common standard single-motion agitators. The end result is a top to bottom gentle blending of the eggshells. Heat and pressure can be applied for washing and sanitizing or standard santizing agents (eg chlorine bleach) can be added. As with the centrifuge, the washing can be done as either a batch or continuous feed. After washing, the shells can be transferred via a de-watering screw auger conveyor (which in many cases provides a useful delivery means for suspensions, especially where de-watering is desired) to a continuous dryer such as those manufactured by Buffalo Technologies Inc. (Buffalo, N.Y.) and used for drying food products (potato chips, cereals, etc.). Dried, clean and santized egg shell can be either stored or fed directly into a high speed particle reduction unit (see below).

For hatchery waste, a mix of live chicks, broken shells and unhatched eggs (infertile or dead embryo) from hatching trays are typically dumped onto a moving belt which has fixed gaps that allow chicks to fall through but retain broken shells and unhatched eggs (U.S. Pat. No. 5,199,380). The chicks are conveyed either to a sexing room, a vaccination area or directly to the boxing area and the shell waste continues on towards a vacuum system. Currently, in a standard hatchery system, the vacuum removes all the material. However, in an example of the process illustrated here, the strength of the vacuum is adjusted to remove only broken shell, leaving the unhatched eggs behind for waste processing. The hatchery waste shells do not require drying prior to the separation of the shell and membrane since they are inherently dry after the chick has hatched. The dried shells are deposited in a storage tank for transfer to a central processing facility for membrane and shell separation. The central facility concept is particularly useful since many of the hatcheries are located in geographic clusters and often involve several companies. Washing and sanitation can occur anytime after the broken shell is separated from the unhatched eggs. If washing/sanitation occurs prior the separation of the shell and non-shell material, the waste shell is typically also dried prior to that separation.

To illustrate more specifically, waste eggshells are received in a hopper from where they are guided into the particle size-reducing device, which characteristically outputs eggshell waste particles of a particular size. A particularly preferable range of particle sizes is between about 0.1 mm to about 15.0 mm, more preferably between 0.25 mm to 10 mm, even better is between 0.5 mm to 4.0 mm with respect to the largest linear dimension of each particle (i.e., the longest edge-to-edge dimension thereof, whether continuous or discontinuous).

The particle size-reducing device useful in the present invention includes, generally, a driving motor and a cutting head. It is a particular feature of the present invention that particle size reducing device not only provides a cutting action by which waste egg shells are reduced to particle sizes as mentioned above, but also typically provides an abrasive effect whereby the linking structure attaching the egg shell membranes to the egg shell is disrupted. A particularly useful example of such a particle size-reducing device is commercially available from Urschel Laboratories Inc. under the trademark "Comitrol." The Comitrol is known in the size reduction field, especially in food sciences. More specifically, an example of a Comitrol unit manufactured by Urschel Labs Inc. is a Model 3600 Comitrol with a 10 HP 220/440 Volt 3 Phase drive on the cutting head. 21.5"× 13.25" top infeed pan with 4.5"×5.25" feed throat opening. 43" infeed height 2" cutting head with 3 blade Dio-cut impeller. 3" diameter powered feed screw powered by 16 HP drive. This machine receives the dried shell waste via a top-loading hopper. Within the Comitrol is a multi-bladed impeller, which rotates at high speed forcing the shell out through a series of slots on the cutting head. The grooves within the cutting head contain thousands of individual sharp blades. The shell impacts the blades and the membrane is stripped from the shell from the cutting and abrading action and the shell particle size is reduced. The type of head determines the amount of the reduction in size. The mixture of separated shell and membrane can be collected in a continuous fashion and conveyed for further processing.

It will be readily appreciated that different, known particle size reducing devices may be used in practicing the invention especially if the aforementioned abrasive effect is still provided (either in the operation of the alternate particle size reducing device or additionally as part of the separating process) to cause the linking structure disruption discussed above.

Isolation of the now separated shell and membrane can be accomplished several ways. Both of the specific methods described use the shell and membranes differing properties of weight and size to isolate each fraction. The shaker sieve method takes advantage of existing technology in the food industry which has built shakers to separate food particles based on weight and size (eg. breaded chicken separated from loose batter, cereal separated from broken or powdered material). An example is shaker sieves manufactured by the FMC Corp. (Chicago, Ill.). Here, the output of the high-speed particle reduction unit is fed directly onto a moving belt, which is vibrating in multiple directions. Directly below this shaker belt is a second conveyor (non-shaking). The lighter and larger membrane remains on the top belt while the smaller, heavier shell drops through to the lower belt. The membrane and shell can be separately fed directly into baggers for recovery or further processing.

One type of further processing would be grinding the pure shell to a powder form. This could be accomplished with a batch mixer and grinder such as a unit from Readco (York, Pa.) which is a dry powder grinding and processing system used for production of antibiotics, vitamins and antacids as well as tile, polyester and polyvinylchloride.

Another method utilizes forced air to separate the membrane and shell components. An example of these types of separators are cyclone-forced air separators which are used to separate mixtures of distinct particle sizes in many industrial Applications. Cyclone separators are generally used on particles above 5 $\mu$m in size. The shell/membrane mixture enters the cyclone from a tangential position for a conventional design or from the top for a vane-axial design. The particle laden mixture stream spirals down the body of the cyclone causing the shell particles to migrate to the cyclone wall where they slide to the bottom and into a collector. The lighter membrane reverses direction and exits upward through the center of the cyclone.

It will be recognized that bioactivity, biohazard, and sanitation issues are important in the method and apparatus disclosed herein according to the present invention, especially in the presence of wet eggshells and membrane. Accordingly, it is noted, especially with regard to the structural elements of the apparatus disclosed herein, that materials of manufacture must generally be chosen in accordance with applicable regulatory standards (such those of the U.S. Department of Agriculture). For example, hoppers, conduits, vessel tanks, augers, drying units and washers may preferably be made from stainless steel.

It is another object of this invention to provide products comprised of the materials separated by the described methods. This includes collagen as well as egg components with nutritional value such as calcitic calcium carbonate as a calcium supplement, other nutritional components found in eggs including but not limited to protein, amino acids, vitamins and collagen. Each of the compositions that can be recovered as described herein can be optionally sanitized and sterilized and provided in a pure form, i.e. without measurable contamination with other materials. Alternatively, each of those compositions can be provided in a form containing trace quantities of one or more other materials of avian origin. By "trace" is meant detectable amounts of the other material(s) but at levels below safety or regulatory thresholds. Compositions containing such trace levels of other avian materials will be suitable for use in humans or other animals or consumption by humans or other animals.

In view of the methods and apparatus disclosed herein, it now becomes practical for the first time to separately isolate collagen and other high value products from eggshell waste using conventional methods. For example, the majority of the collagens in eggshell membrane can be recovered using limited digestion with pepsin or other proteolytic enzymes under conditions permitting limited digestion, e.g. in 0.5 M acid acetic, pH 3.0. Digestion occurs for at least 2 hours and preferably up to 12 hours. Using this method partially degrades the collagen allowing it to be solubilized while completely degrading other protein types. The solubilized collagen can undergo serial salt fractionations at acid pH conditions for preferential precipitation of different types of collagen using a range of 0.5M to 1.5M NaCl. Precipitated collagen can be centrifuged to separate it from non-precipitated material, re-dissolved in acid-containing solutions and precipitated with a salt solution, preferably NaCl. This procedure can be repeated several times to purify the collagen. Further purification of the collagens recovered in the selective precipitation procedures can be achieved by chromatography on carboxymethyl-cellulose in native form (Miller E. J., 1982, Meth. Enzymol., 82:61). This procedure can resolve the collagen fractions based on salt-gradient elution.

In another example, it is well known that protein-containing material can be reduced to individual amino acids by the application of heat (100C) at an acid pH (<2.0). The individual amino acids can be isolated using conventional High Pressure Liquid Chromatography separating molecules based on charge and/or hydrophobicity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The full disclosure of each of the patent documents and scientific papers cited herein is hereby incorporated by reference. Those documents serve to illustrate the state of the art in various aspects of this invention. Numerous modifications and variations of the present invention should be apparent to one of skill in the art. Such modifications and variations, including the practitioner's routine design choices in the design and assembly of the device or execution of the method of the invention, as defined in the claims which follow, are intended to be encompassed by the scope of the invention and of the appended claims.

TABLE 1

Comparison of the percentages of total protein and individual amino acids found in eggshell membrane and other conventional protein sources.

| | % | | |
| --- | --- | --- | --- |
| | Eggshell Membrane | Casein | Isolated Soy |
| Protein | 85 | 85 | 87 |
| Lysine | 3.35 | 7.00 | 4.90 * |
| Histidine | 3.48 | 2.60 | 2.10 * |
| Arginine | 6.46 | 3.30 | 5.90 * |
| Threonine | 4.60 | 3.90 | 2.90 |
| Glutamic Acid | 9.70 | 22.40 | 17.70 |
| Proline | 9.34 | 10.60 | 5.60 |
| Glysine | 4.94 | 1.50 | 3.30 |
| Cysteine | 8.50 | 0.26 | 1.20 * |
| Valine | 6.30 | 6.40 | 4.00 * |
| Methionine | 3.09 | 2.80 | 1.10 * |
| Isoleucine | 3.19 | 5.40 | 3.90 * |
| Leucine | 4.30 | 8.70 | 6.90 * |
| Tyrosine | 1.73 | 4.40 | 3.30 |
| Phenylalanine | 1.65 | 4.70 | 4.60 |
| Tryptophan | — | 0.95 | 1.10 |

* Essential Amino Acids

What is claimed is:

1. A method for separately recovering the shell and non-shell components from chicken hatchery eggshell waste, comprising the steps of:
   a. providing an initial mixture of hatchery waste shells, live chicks, and unhatched eggs to a chick harvesting assembly and a vacuum suction system;
   b. using the vacuum suction system to recover the hatchery waste shells from said live chicks and unhatched eggs;

c. processing said hatchery waste shells to
   (i) reduce their particle size, or,
   (ii) dislodge at least part of the membrane from the eggshell thereof, or,
   (iii) both (i) and (ii),
   to yield a processed eggshell waste mixture; and,
d. separately recovering the shell components, the non-shell components or both, from the processed eggshell waste mixture.

2. The method of claim 1 wherein said hatchery waste shells are processed using a particle size reduction apparatus, which mechanically reduces particle size.

3. The method of claim 1 wherein said hatchery waste shells are processed using a slicer, dicer, strip cutter, shredder, grinder, granulator, mill, comminutor, abrader, pulverizer, crusher, compactor, blender or sonicator apparatus.

4. The method of claim 2 wherein the apparatus is a high impact particle reduction apparatus.

5. The method of claim 1 which further comprises the step of washing the hatchery waste shells to remove part or all of any residual materials other than those of eggshell origin prior to processing the initial mixture.

6. The method of claim 1 wherein the shell and non-shell components are separately recovered based on their respective differences in physical properties.

7. The method of claim 6 wherein the shell and non-shell components are separately recovered using a vibrating or shaking device to separate relatively larger, lighter or less dense components from smaller, heavier or denser components.

8. The method of claim 7 wherein the shell and non-shell components are separately recovered using a shaker-sieve belt.

9. The method of claim 6 wherein the shell and non-shell components are separately recovered using a stream of gas to separate relatively larger, lighter or less dense components from smaller, heavier or denser components.

10. The method of claim 9 wherein the shell and non-shell components are separately recovered using a cyclone forced-air separator.

11. The method of any of claims 1, 2–4 or 5–9 which further comprises the step of washing the separately recovered shell components to remove part or all of any residual non-shell materials.

12. The method of claim 11 which further comprises purifying the washed shell component to yield calcitic calcium carbonate containing trace amounts of avian products, suitable for human consumption.

13. The method of claim 12, which further comprises the step of sterilizing the separately recovered shell component.

14. The method of claim 13, which further comprises the step of recovering collagen from the separately recovered non-shell component.

15. A product produced by the method of claim 1, 3–5 or 7–11, which is comprised of avian eggshell membrane.

16. A product produced by the method of claim 1, 2–4 or 7–11, which is comprised of avian egg protein, separately recovered from the membrane component.

17. A method for separately recovering the shell and non-shell components from chicken hatchery eggshell waste, comprising the steps of:
   a. providing an initial mixture of hatchery waste shells, live chicks, and unhatched eggs to a chick harvesting assembly and a vacuum suction system;
   b. using the vacuum suction system to recover the hatchery waste shells from said live chicks and unhatched eggs;
   c. using a vibrating or shaking device to separate relatively larger, lighter or less dense shell and non-shell components from smaller, heavier or denser shell and non-shell components;
   d. processing said hatchery waste shells to
      (i) reduce their particle size
   to yield a processed eggshell waste mixture; and,
   e. separately recovering the shell components, the non-shell components or both, from the processed eggshell waste mixture.

18. A device for separately recovering the shell and non-shell components from chicken hatchery eggshell waste, comprising:
   a. a delivery apparatus for providing an initial mixture of hatchery waste shells, live chicks, and unhatched eggs to a chick harvesting assembly and a vacuum suction system;
   b. a vacuum suction system for recovering the hatchery waste shells from said live chicks and unhatched eggs;
   c. a processing apparatus for processing said hatchery waste shells to
      (i) reduce their particle size, or,
      (ii) dislodge at least part of the membrane from the eggshell thereof, or,
      (iii) both (i) and (ii),
   to yield a processed eggshell waste mixture; and,
   d. a separation apparatus for separately recovering the shell components, the non-shell components or both, from the processed eggshell waste mixture.

19. The device of claim 18 in which the delivery apparatus is a feed tube, conveyor apparatus or storage apparatus disposed for delivery of the initial mixture of hatchery waste shells, live chicks, and unhatched eggs to a chick harvesting assembly and a suction system.

20. The device of claim, 18 or 19 which further comprises a moisture reducing apparatus, disposed either between the processing apparatus and the separation apparatus or between the delivery apparatus and the processing apparatus.

21. The device of claim 18 in which the processing apparatus mechanically reduces particle size.

22. The device of claim 18 in which the processing apparatus is a slicer, dicer, strip cutter, shredder, grinder, granulator, mill, comminutor, abrader, pulverizer, crusher, compactor, blender or sonicator apparatus.

23. The device of claim 18 in which the processing apparatus is a high impact particle reduction apparatus.

24. The device of claim 18 or 19 which further comprises a washing apparatus disposed between the delivery apparatus and the processing apparatus, for washing the hatchery waste shells to remove part or all of any residual materials other than those of eggshell origin prior to processing the initial mixture.

25. The device of claim 18, wherein the separation apparatus separates shell and non-shell components based on their respective differences in physical properties.

26. The device of claim 25 wherein the separation apparatus is a vibrating or shaking device to separate relatively larger, lighter or less dense components from smaller, heavier or denser components.

27. The device of claim 26 wherein the separation apparatus is a shaker-sieve belt.

28. The device of claim 25 wherein the separation apparatus uses a stream of gas to separate relatively larger, lighter or less dense components from smaller, heavier or denser components.

29. The device of claim 28 wherein the separation apparatus is a cyclone forced-air separator.

30. The device of claim 18 or 25 which further comprises a washing apparatus disposed after the separation apparatus for removing part or all of any residual non-shell materials from the separately recovered shell component.

31. The device of claim 18 or 25 which further comprises a sterilizing apparatus disposed after the separation apparatus for sterilizing one or more of the separately recovered components.

32. A method for separately recovering the shell and non-shell components from chicken hatchery eggshell waste, comprising the steps of:
  a. providing an initial mixture of hatchery waste shells, live chicks, and unhatched eggs to a chick harvesting assembly and a vacuum suction system;
  b. using the vacuum suction system to recover the hatchery waste shells from said live chicks and unhatched eggs;
  c. using a stream of gas to separate relatively larger, lighter or less dense shell and non-shell components from smaller, heavier or denser shell and non-shell components;
  d. processing said hatchery waste shells to reduce their particle size, to yield a processed eggshell waste mixture; and,
  e. separately recovering the shell components, the non-shell components or both, from the processed hatchery eggshell waste mixture.

33. A device for separately recovering the shell and non-shell components from chicken hatchery eggshell waste, comprising:
  a. a delivery apparatus for providing an initial mixture of hatchery waste shells, live chicks, and unhatched eggs to a chick harvesting assembly and a vacuum suction system;
  b. a vacuum suction system for recovering the hatchery waste shells from said live chicks and unhatched eggs;
  c. a vibrating or shaking device to separate relatively larger, lighter or less dense shell and non-shell components from smaller, heavier or denser shell and non-shell components;
  d. a processing apparatus for processing said hatchery waste shells to reduce their particle size, to yield a processed eggshell waste mixture; and,
  e. a separation apparatus for separately recovering the shell components, the non-shell components or both, from the processed eggshell waste mixture.

34. A device for separately recovering the shell and non-shell components from chicken hatchery eggshell waste, comprising:
  a. a delivery apparatus for providing an initial mixture of hatchery waste shells, live chicks, and unhatched eggs to a chick harvesting assembly and a vacuum suction system;
  b. a vacuum suction system for recovering the hatchery waste shells from said live chicks and unhatched eggs;
  c. a gas-emitting device for separating relatively larger, lighter or less dense shell and non-shell components from smaller, heavier or denser shell and non-shell components;
  d. a processing apparatus for processing said hatchery waste shells to reduce their particle size, to yield a processed eggshell waste mixture; and,
  e. a separation apparatus for separately recovering the shell components, the non-shell components or both, from the processed eggshell waste mixture.

* * * * *